United States Patent
Hoogenboom et al.

(10) Patent No.: US 10,869,930 B2
(45) Date of Patent: Dec. 22, 2020

(54) POLY(CYCLIC IMINO ETHER)S

(71) Applicant: UNIVERSITEIT GENT, Ghent (BE)

(72) Inventors: Richard Hoogenboom, Terneuzen (NL); Bart Verbraeken, Lummen (BE)

(73) Assignee: UNIVERSITEIT GENT, Ghent (BE)

( * ) Notice: Subject to any disclaimer, the term of this patent is extended or adjusted under 35 U.S.C. 154(b) by 59 days.

(21) Appl. No.: 16/312,219

(22) PCT Filed: Jul. 3, 2017

(86) PCT No.: PCT/EP2017/066489
§ 371 (c)(1),
(2) Date: Dec. 20, 2018

(87) PCT Pub. No.: WO2018/002382
PCT Pub. Date: Jan. 4, 2018

(65) Prior Publication Data
US 2019/0231889 A1    Aug. 1, 2019

(30) Foreign Application Priority Data
Jul. 1, 2016    (EP) ..................................... 16177411

(51) Int. Cl.
*A61K 47/59*    (2017.01)
*C08G 73/02*    (2006.01)
(Continued)

(52) U.S. Cl.
CPC .......... *A61K 47/59* (2017.08); *A61K 47/6907* (2017.08); *A61K 48/0008* (2013.01); *C08G 73/0233* (2013.01); *C12N 15/87* (2013.01)

(58) Field of Classification Search
CPC ............................ C08G 73/0233; A61K 47/59
See application file for complete search history.

(56) References Cited

U.S. PATENT DOCUMENTS

| | | | |
|---|---|---|---|
| 3,516,944 A * | 6/1970 | Litt | ............ C10M 5/00 524/386 |
| 2011/0165258 A1* | 7/2011 | Kabanov | ............ A61P 35/00 424/497 |
| 2015/0025196 A1* | 1/2015 | Hoogenboom | ...... A61K 51/065 525/54.1 |

FOREIGN PATENT DOCUMENTS

| JP | 2643403 B2 * | 8/1997 |
|---|---|---|
| WO | WO 2009/156180 A3 | 12/2009 |
| WO | WO 2013/103297 A1 | 7/2013 |

OTHER PUBLICATIONS

Kobayashi et al., "Block Copolymer from Cylic Imino Ethers: A New Class of Nonionic Polymer Surfactant", Macromolecules, vol. 19, No. 15, Jan. 1, 1986, pp. 535-541.
(Continued)

*Primary Examiner* — Mark S. Kaucher
(74) *Attorney, Agent, or Firm* — Foley & Lardner LLP; Sunit Talapatra

(57) ABSTRACT

The invention relates to invention relates to a statistical copolymer represented by the following formula (I): Ini-[Ox]$_m$-[Oz]$_n$-Nuc (I) wherein: Ini represents a residue of an initiator of cationic polymerization, Nuc represents a residue of a nucleophilic agent, Ox represents N(R$^1$)CHR$^a$CHR$^a$; each R$^1$ independently represents H or C(O)R$^{11}$; and R$^{11}$ independently represents optionally substituted C$_{1-12}$ alkyl, optionally substituted cycloalkyl, optionally substituted aralkyl or optionally substituted aryl; Oz represents N(R$^2$)CHR$^a$CHR$^a$CHR$^a$; each R$^2$ independently represents C(O)R$^{21}$ or H; and R$^{21}$ independently represents optionally substituted C$_{1-12}$ alkyl, optionally substituted cycloalkyl, optionally substituted aralkyl or optionally substituted aryl; each R$^a$ independently represents H, linear or branched C$_{1-3}$ alkyl; m≥5; n≥5; m+n≥20; 3:97≤m:n≤97:3. The statistical copolymers of the present invention exhibit useful properties
(Continued)

33 Subunits     33 Subunits that can be exploited in the medical field, especially in polymer micelles for drug delivery and polyplexes for DNA delivery.

11 Claims, 7 Drawing Sheets

(51) Int. Cl.
    *A61K 47/69*     (2017.01)
    *C12N 15/87*     (2006.01)
    *A61K 48/00*     (2006.01)

(56)         References Cited

OTHER PUBLICATIONS

Bolksma et al., "Poly(cyclic imino ether)s Beyond 2-Substituted-2-oxazolines", Macromolecular Rapid Communications, vol. 32, No. 18, Jun. 28, 2011, pp. 1419-1336.
International Search Report issued in PCT/EP2017/066489, dated Sep. 15, 2017.
Written Opinion of the International Searching Authority issued in PCT/EP2017/066489, dated Sep. 15, 2017.

\* cited by examiner

POLY(CYCLIC IMINO ETHER)S

CROSS-REFERENCE TO RELATED APPLICATIONS

This application is the National Phase of International Patent Application No. PCT/EP2017/066489, filed Jul. 3, 2017, published on Jan. 4, 2018 as WO 2018/002382 A1, which claims priority to European Application No. 16177411.2, filed Jul. 1, 2016. The contents of these applications are herein incorporated by reference in their entirety.

TECHNICAL FIELD OF THE INVENTION

The present invention relates to poly(cyclic imino ether)s. More particularly, the invention relates to statistical copolymers of 2-oxazoline monomers and 2-oxazine monomers.

The copolymers of the present invention exhibit useful properties that can be exploited in the medical field, especially polymer therapeutics such as micellar drug delivery systems and polyplexes.

The invention also provides a method of preparing a statistical copolymer by cationic ring-opening polymerization of a monomeric reaction mixture comprising an optionally 2-substituted 2-oxazoline and an optionally 2-substituted 2-oxazine.

BACKGROUND OF THE INVENTION

Polymer therapeutics include rationally designed macromolecular drugs, polymer-drug and polymer-protein conjugates, polymeric micelles containing covalently or noncovalently bound drug, and polyplexes for DNA delivery.

Polymer micelles have been used widely in the delivery of various therapeutic drugs. Polymer micelles consisting of amphiphilic block copolymers form a hydrophobic core, in which lipophilic drugs can be physically incorporated. Hydrophilic blocks or segments generate water-friendly corona and encapsulate the hydrophobic core. In this way, poorly soluble drugs can be successfully solubilized in aqueous media.

Gene therapy is a promising new tool to treat some diseases that currently are incurable such as, genetic disorders, cancer diseases and some retinal diseases. The basic idea in gene therapy is straightforward: the failure to produce some protein coded by a defective gene is overcome by delivering a new intact gene into the nucleus of the cells. Since naked DNA as such is not usually efficiently internalized by cells, a carrier system (vector) is needed for gene delivery. Delivery methodologies have included the use of recombinant viruses and synthetic materials, especially cationic polymers. While viruses are the most efficient delivery vehicles currently available, polymers exhibit several properties—including very flexible chemistry, potential for biocompatibility, simplicity, and inexpensive synthesis—that make them excellent candidates for the gene delivery vehicles.

Stimuli-responsive polymers (or intelligent polymers) have great potential as nonviral vectors to obtain site-, timing-, and duration period-specific gene expression. Stimuli responsive polymers have sharp and reversible responses to small changes in environmental conditions such as temperature, pH, light, ionic strength, electric and magnetic fields, and they have emerged as a class of materials known as "smart" materials. pH- and temperature-responsive polymers are the two most popular members of the intelligent polymer systems. Polymers having pH responsivity character generally consist of a hydrophobic monomer and an ionizable comonomer having more hydrophilic nature. Change in pH and therefore in the net charge causes the phase change depending on hydrophobic and hydrophilic balance of the copolymer. Typical examples are the copolymers of methylmethacrylate (MMA) with methacrylic acid (MAc) or dimethylaminoethyl methacrylate (DMAEMA). MMA is the hydrophobic section while MAc is the hydrophilic part of the chains. MAc is hydrophilic at high pH when COOH groups are deprotonated, but becomes more hydrophobic when —COOH groups are protonated. The copolymers of MMA with DMAEMA, which is hydrophilic at low pH, when amino groups are protonated but more hydrophobic when amino groups are deprotonated. These copolymers are soluble at low pH but precipitate at slightly alkaline conditions.

Poly(cyclic imino ether)s of various architectures and chemical functionalities can be prepared in a living and therefore controlled manner via cationic ring-opening polymerization (CROP). 2-Oxazolines are 5-membered cyclic imino ethers whose cationic ring-opening polymerization mechanism and resulting polymer properties have been extensively studied. However, also 6-membered cyclic imino ethers (2-oxazines) and 7-membered cyclic imino ethers (2-oxazepines) can be polymerized via CROP Polyoxazolines have found widespread applications, ranging from coatings to pigment dispersants. Furthermore, several polyoxazolines are water-soluble or amphiphilic and relatively non-toxic, which makes them interesting as biomaterials.

Not only homopolymers of polyoxazolines, but also block copolymers and statistical copolymers of polyoxazolines are known in the art.

Hruby et al. (*Polyoxazoline Thermoresponsive Micelles as Radionuclide Delivery Systems*, Macromol. Biosci. 2010, 10(8), 916-924) describe the synthesis of ABA triblock copolymers poly[2-methyl-2-oxazoline-block-(2-isopropyl-2-oxazoline-co-2-butyl-2-oxazoline)-block-2-methyl-2-oxazoline]. The phenolic moiety introduced into the copolymer allowed radionuclide labeling with iodine-125 ongoing in good yield with sufficient in vitro stability under model conditions.

WO 2009.156180 describes polymeric delivery systems for active agents comprising:
a) at least one copolymer comprising:
first repeating units represented by [N(CO)(R$^A$)CH$_2$CH$_2$]— wherein R$^A$ is a hydrocarbon group, optionally substituted with —OH, —SH, —COOH, —NR'$_2$, —COOR', —CONR', —CHO, with R' representing H or C$_{1-3}$ alkyl, and with R$^A$ being selected such that the first repeating units are hydrophilic; and
second repeating units represented by —[N(CO)(R$^B$)CH$_2$CH$_2$]— wherein R$^B$ is a hydrocarbon group optionally substituted with halogen, —OH, —SH, —COOH, —NR"$_2$, —COOR", —CONR", —CHO, with R" representing H, alkyl or alkenyl, and with R$^B$ being selected such that the second repeating units are more hydrophobic than the first repeating units; and
b) one or more active agent(s).

WO 2013/103297 relates to poly(2-oxazoline) polymers. Example 4 describes copolymerization of (2-methoxycarbonylethyl)-2-oxazoline with 2-ethyl-2-oxazoline or 2-methyl-2-oxazoline to produce a statistical copolymer.

Schultz et al. (Drug-Induced Morphology Switch in Drug Delivery Systems Based on Poly(2-oxazoline)s, ACS Nano, 2014 Mar. 25; 8(3):2686-96) incorporated paclitaxel into micelles of amphiphilic ABA poly(2-oxazoline) triblock copolymers. The hydrophilic blocks A comprised poly(2-methyl-2-oxazoline) while the middle blocks B were either just barely hydrophobic poly(2-n-butyl-2-oxazoline) or highly hydrophobic poly(2-n-nonyl-2-oxazoline). Lambermont-Thijs et al. (*Efficient Cationic Ring-Opening Polymerization of Diverse Cyclic Imino Ethers: Unexpected Copolymerization Behavior*, Macromolecules 2011, 44, 4320-4325) describe copolymerization of 4-ethyl-2-butyl-2-oxazoline with 2-methyl-2-oxazoline and/or 2-phenyl-2-oxazoline. Kinetic analysis of this copolymerization revealed the formation of a gradient copolymer structure going from a 2-methyl-2-oxazoline rich domain, via a 4-ethyl-2-butyl-2-oxazoline rich domain to a 2-phenyl-2-oxazoline rich domain at the final stages of the polymerization.

Jaksch et al. (*The collapse and aggregation of thermoresponsive poly(2-oxazoline) gradient copolymers: a time-resolved SANS study*, Colloid Polym Sci (2014) 292:2413-2425) describe the synthesis of gradient copolymers of iso-propyl-2-oxazoline and n-nonyl-2-oxazoline.

Block copolymers of oxazolines and oxazines are also known.

Kobayashi et al. (*Block copolymer from cyclic imino ethers: a new class of nonionic polymer surfactant*. Macromolecules. 1986, v. 19, n. 15, 535-541) describes block copolymers formed from cyclic imino ethers prepared by utilizing cationic ring-opening polymerization of 2-substituted 2-oxazolines in combination with unsubstituted or 2-substituted 5,6-dihydro-4H-1,3-oxazines using a sequential monomer additional protocol.

Bloksma et al. (*Poly(cyclic imino ether)s Beyond 2-Substituted-2-oxazolines*, Macromol. Rapid Commun. 2011, 32, 1419-1441) provide an overview on the polymerizations of 2-oxazine (2-OZI) and chiral 4- and 5-substituted 2-oxazoline (2-OZO) as well as of selected properties of the resulting polymers. The authors describe the preparation of a block copolymer of 2-methyl-2-OZO and 2-phenyl-2-OZI, a block copolymer of 2-phenyl-2-OZO and 2-methyl-2-OZI and a block copolymer 2-phenyl-2-OZO and 2-unsubstituted-2-OZI.

U.S. Pat. No. 5,854,331 describes block copolymers of oxazolines and oxazines as pigment dispersants and their use in ink jet inks. The block polymer dispersants are selected from the group consisting of AB, ABA, and BAB block copolymers wherein the A block is hydrophobic, and the B block is hydrophilic; said block polymeric dispersant being comprised of monomers selected from the group consisting of 2-substituted oxazoline monomers, 2-substituted oxazine monomers, and mixtures thereof.

SUMMARY OF THE INVENTION

The inventors have discovered that poly(cyclic imino ether)s having desirable properties can be produced without great difficulty by statistical polymerization of a monomeric reaction mixture that contains 2-oxazoline monomer as well as 2-oxazine monomer.

Thus, one aspect of the invention relates to a statistical copolymer represented by the following formula (I):

Ini-[Ox]$_m$-[Oz]$_n$-Nuc    (I)

wherein:
Ini represents a residue of an initiator of cationic polymerization,
Nuc represents a residue of a nucleophilic agent,
Ox represents N(R$^1$)CHR$^a$CHR$^a$; each R$^1$ independently represents H or C(O)R$^{11}$; and R$^{11}$ independently represents optionally substituted C$_{1-12}$ alkyl, optionally substituted cycloalkyl, optionally substituted aralkyl or optionally substituted aryl;
Oz represents N(R$^2$)CHR$^a$CHR$^a$CHR$^a$; each R$^2$ independently represents C(O)R$^{21}$ or H; and R$^{21}$ independently represents optionally substituted C$_{1-12}$ alkyl, optionally substituted cycloalkyl, optionally substituted aralkyl or optionally substituted aryl;
each R$^a$ independently represents H, linear or branched C$_{1-3}$ alkyl;
m≥5;
n≥5;
m+n≥20;
3:97≤m:n≤97:3.

The statistical copolymers of the present invention exhibit useful properties that can be exploited in the medical field, especially in polymer micelles for drug delivery and polyplexes for DNA delivery.

The present invention also provides a method of preparing a statistical copolymer, said method comprising cationic ring-opening polymerization of a monomeric reaction mixture comprising an optionally 2-substituted 2-oxazoline and an optionally 2-substituted 2-oxazine in a molar ratio in the range of 3:97 to 97:3, wherein the optional substituent in the 2-position of each of the 2-substituted-2-oxazoline and the 2-substituted-2-oxazine is independently selected from C$_{1-12}$ alkyl, optionally substituted cycloalkyl, optionally substituted aralkyl or optionally substituted aryl.

The inventors have found that the monomeric composition of the statistical copolymer and consequently the properties of the copolymer can easily be manipulated by selecting different combinations of optionally 2-substituted 2-oxazoline and optionally 2-substituted 2-oxazine. Both the substituent in the 2-position of the 2-oxazoline and the substituent in the 2-position of the 2-oxazine have a significant effect on the participation of these monomers in the copolymerization reaction. Thus, random copolymers may be produced, for instance, by selecting a 2-substituted-2-oxazoline and a 2-substituted-2-oxazine that are equally reactive during copolymerization. Random copolymers are particularly suitable for polyplex formation, especially if the copolymer is a polycationic polymer.

Gradient polymers on the other hand may be produced by selecting a 2-oxazoline and a 2-oxazine that exhibit clearly different reactivity during copolymerization. By selecting a 2-oxazoline/2-oxazine combination with a relatively low difference in reactivity, a gradient copolymer may be produced that exhibits a slow gradual change in monomeric composition across the chain. By selecting a 2-oxazoline/2-oxazine combination with a substantial difference in reactivity, a gradient copolymer may be produced that exhibits a much more steep change in monomeric composition across the chain.

The gradual change in composition of gradient copolymers results in a reduced interchain repulsion compared to block copolymers. Theoretical studies have predicted that the degree of composition variation in gradient copolymers can be altered through the monomer distribution and that they will organize into sinusoidal composition profiles, rather than the step-like profiles seen for block copolymers. This results in a wide range of possible local environments, rather than the one or two seen in random and block copolymers.

The present invention also relates to the application of the statistical copolymers of the present invention in micellar drug delivery systems or polyplexes.

DETAILED DESCRIPTION OF THE INVENTION

Figure 1:
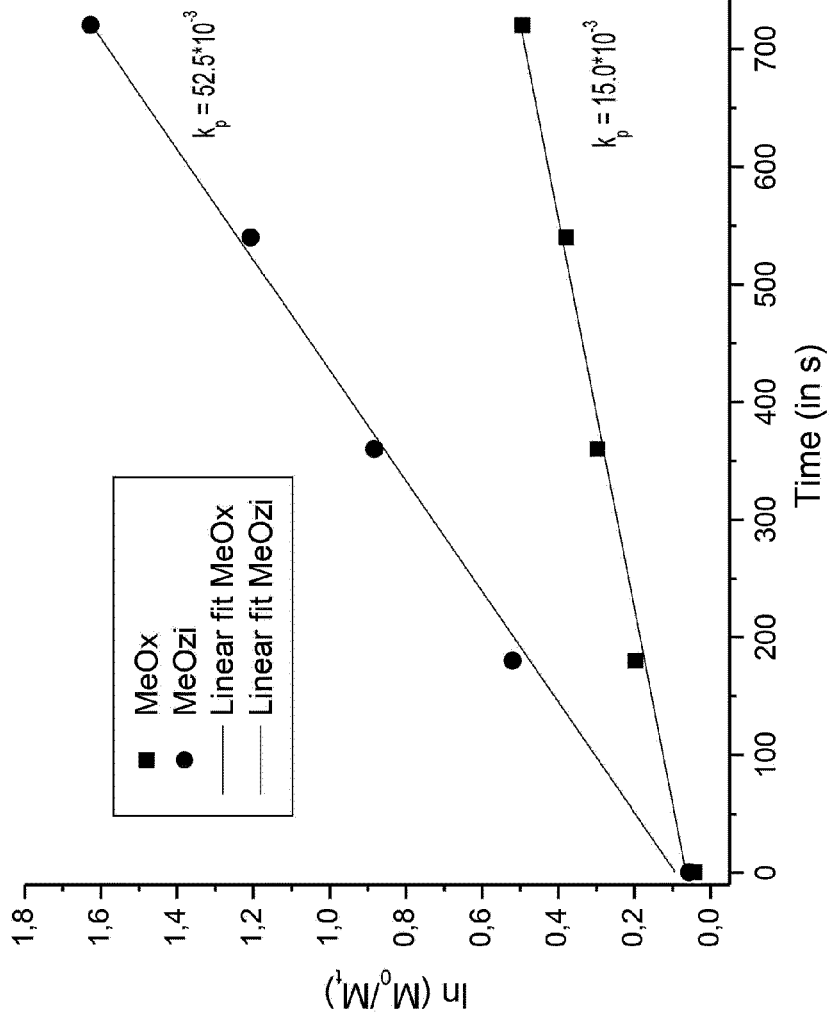
FIG. 1 is a kinetic plot of one copolymerization of 2-Methyl-2-oxazoline (MeOx) and 2-methyl-2-oxazine (MeOZi).

Accordingly, a first aspect of the present invention relates to a statistical copolymer represented by the following formula (I):

Ini-[Ox]$_m$-[Oz]$_n$-Nuc     (I)

wherein:
Ini represents a residue of an initiator of cationic polymerization,
Nuc represents a residue of a nucleophilic agent,
Ox represents N(R$^1$)CHR$^a$CHR$^a$; each R$^1$ independently represents H or C(O)R$^{11}$; and R$^{11}$ independently represents optionally substituted C$_{1-12}$ alkyl, optionally substituted cycloalkyl, optionally substituted aralkyl or optionally substituted aryl;
Oz represents N(R$^2$)CHR$^a$CHR$^a$CHR$^a$; each R$^2$ independently represents C(O)R$^{21}$ or H; and R$^{21}$ independently represents optionally substituted C$_{1-12}$ alkyl, optionally substituted cycloalkyl, optionally substituted aralkyl or optionally substituted aryl;
each R$^a$ independently represents H, linear or branched C$_{1-3}$ alkyl;
m≥5;
n≥5;
m+n≥20;
3:97≤m:n≤97:3.

The term "statistical copolymer" as used herein refers to copolymers in which the sequence of monomer residues follows a statistical rule.

The term "random copolymer" as used herein refers to a statistical copolymer in which the probability of finding a given type monomer residue at a particular point in the chain is similar to the mole fraction of that monomer residue in the chain.

The term "gradient copolymer" as used herein refers to a statistical polymer that exhibits a gradual change in monomeric composition along the chain. This arrangement is different from random copolymers, which maintain a constant average composition along the chain, and block copolymers, which change abruptly along the chain.

The statistical copolymers of the present invention can suitably be characterized by comparing the monomeric compositions of different fragments of the copolymer. To this end the copolymer is divided in 3 equal fragments, i.e. a fragment adjacent Ini (Ini fragment), a fragment adjacent Nuc (Nuc fragment) and a central fragment that separates the Ini fragment and the Nuc fragments. In case the total number of monomeric units is no multiple of 3, the size of the central fragment is chosen such that the Ini fragment and the Nuc fragment are of equal size. In the following table a few arithmetic examples are provided.

| | Number of monomeric units | | |
|---|---|---|---|
| Polymer | Ini fragment | Central fragment | Nuc fragment |
| 98 | 33 | 32 | 33 |
| 99 | 33 | 33 | 33 |
| 100 | 33 | 34 | 33 |

In case of random copolymers the monomeric composition of the Ini fragment and the Nuc fragment are quite similar, whereas in case of gradient copolymers, the monomeric compositions of these fragment are dissimilar.

In aforementioned formula (I) preferably each R$^a$ independently represents H or methyl. Most preferably, represents H, In one embodiment of the present invention at least 50%, preferably at least 70% and more preferably at least 90% of the R$^1$ residues is C(O)R$^{11}$.

In an alternative embodiment of the invention more than 50% of the R$^1$ residues is H. Preferably, more than 70% and more preferably more than 90% of the R$^1$ residues is H. As will be explained below, copolymers according to the present invention in which a large fraction of the R$^1$ residues is H can be synthesized by polymerizing a monomeric reaction mixture containing oxazoline monomers, followed by hydrolytic removal of the pendant acyl groups from the oxazoline units in the copolymer.

In a further embodiment, at least 50%, preferably at least 70% and more preferably at least 90% of the R$^2$ residues is C(O)R$^{21}$.

In an alternative embodiment, more than 50%, preferably more than 70% and most preferably more than 90% of the R$^2$ residues is H. Copolymers according to the present invention in which a large fraction of the R$^2$ residues is H can be synthesized by polymerizing a monomeric reaction mixture containing oxazine monomers, followed by hydrolytic removal of the pendant acyl group from the oxazine units in the copolymer.

The copolymer of the present invention typically contains at least 5 oxazoline units ([Ox]). Accordingly, in a preferred embodiment the integer m in formula (I) is at least 5, more preferably at least 10 and most preferably at least 20. Typically the integer m does not exceed 250.

The number of oxazine units ([Oz]) in the present copolymer typically is at least 5. In other words, the integer n in formulate (I) preferably is at least 5. More preferably the integer n is at least 10, and most preferably n is at least 20. Typically the integer n does not exceed 250.

The combination of oxazoline units and oxazine units the copolymer of the present invention typically is at least 20 (m+n≥20). More preferably, m+n≥30 and most preferably m+n≥50. The combination of oxazoline units and oxazine units in the copolymer of the present invention typically does not exceed 500 (m+n≤500).

Oxazoline units and oxazine units as defined herein are typically present in the statistical copolymer of the present invention in a ratio of 5:95 to 95:5, more preferably in a ratio of 10:90 to 90:10 and most preferably in a ratio of 20:80 to 80:20.

The copolymer of the present invention may contain other monomeric units besides the oxazoline units and oxazine units as defined herein. Preferably the oxazoline units and oxazine units together represent the bulk of all the monomeric units present in the copolymer.

In other words, if the total number of monomeric units in the copolymer is represented by the integer t, the copolymer meets the following condition: (m+n)/t>0.5. More preferably, (m+n)/t>0.7, most preferably (m+n)/t>0.9.

One embodiment of the present invention relates to a statistical copolymer in the form of a random copolymer. The inventors have unexpectedly found that random copolymers can be produced from combinations of oxazoline and oxazine monomers that have substantially different individual polymerization rates, because surprisingly some of these combinations are equally reactive during copolymerization. p Typically, in case of a random copolymer the monomer ratio [Oz]/[Ox] in the Ini fragment and the Nuc fragment differ by no more than a factor 2. More preferably, in case of the random copolymer these ratios do not differ by more than a factor 1.75, most preferably by not more than a factor 1.5.

In the random copolymer of the present invention preferably each $R^{11}$ independently represents methyl, ethyl, cyclopropyl, n-propyl or n-butyl. More preferably, each $R^{11}$ independently represents methyl, ethyl or cyclopropyl Most preferably, each $R^{11}$ independently represents methyl or ethyl.

Each $R^{21}$ in the random copolymers of the present invention preferably independently represents methyl, ethyl, n-propyl, isopropyl or cyclopropyl, n-butyl or n-nonyl. More preferably, each $R^{21}$ independently represents ethyl, n-propyl or isopropyl. Most preferably, each $R^{21}$ independently represents ethyl or isopropyl.

According to a particularly preferred embodiment of the present invention the statistical copolymer is a random copolymer, wherein:
  at least 80% of the $R^{11}$ residues is methyl and at least 80% of the $R^{21}$ residues is iso-propyl; or
  at least 80% of the $R^{11}$ residues is ethyl and at least 80% of the $R^{21}$ residues is iso-propyl; or
  at least 80% of the $R^{11}$ residues is cyclopropyl and at least 80% of the $R^{21}$ residues is methyl; or
  at least 80% of the $R^{11}$ residues is cyclopropyl and at least 80% of the $R^{21}$ residues is ethyl.

According to another advantageous embodiment of the present invention the statistical copolymer is a gradient copolymer wherein the monomer ratio [Oz]/[Ox] in the Ini fragment is at least 2 times higher or lower than the same ratio in the Nuc-fragment of the copolymer. More preferably, in case of the gradient polymer these two ratios differ by at least a factor 3, most preferably by at least a factor 5. Typically these two ratios do not differ by more than a factor 20 in the gradient polymers of the present invention.

The inventors have unexpectedly discovered that it is possible to prepare a gradient polymer in which the oxazine monomeric units are overrepresented in the Ini-fragment of the copolymer relative to the Nuc-fragment of the copolymer despite the fact that the polymerization reactivities oxazine monomers are typically significantly lower than the polymerization reactivities of oxazoline monomers. Accordingly, in a particularly preferred embodiment the statistical copolymer of the present invention is a gradient copolymer wherein the monomer ratio [Oz]/[Ox] in the Ini-fragment of the copolymer is at least 2 times higher, more preferably at least 3 time higher and most preferably 5 to 10 times higher than the same ratio in the Nuc-fragment of the copolymer.

Preferably, each $R^{11}$ in the gradient copolymer of the present invention independently represents optionally substituted $C_{1-9}$ alkyl. More preferably, each $R^{11}$ in the gradient independently represents . . . , most preferably each $R^{11}$ independently represents . . . .

In the gradient copolymer of the present invention typically each $R^{21}$ independently represents optionally substituted $C_{1-9}$ alkyl, more preferably each $R^{21}$ independently represents ethyl, n-propyl, isopropyl, n-butyl or n-nonyl, most preferably each $R^{21}$ independently represents n-propyl, n-butyl or n-nonyl.

According to a particularly preferred embodiment of the present invention the statistical copolymer is a gradient copolymer, wherein:
  at least 80% of the $R^{11}$ residues is methyl and at least 80% of the $R^{21}$ residues is methyl; or
  at least 80% of the $R^{11}$ residues is ethyl and at least 80% of the $R^{21}$ residues is ethyl; or
  at least 80% of the $R^{11}$ residues is n-propyl and at least 80% of the $R^{21}$ residues is n-propyl; or
  at least 80% of the $R^{11}$ residues is n-propyl and at least 80% of the $R^{21}$ residues is ethyl; or
  at least 80% of the $R^{11}$ residues is n-propyl and at least 80% of the $R^{21}$ residues is methyl; or
  at least 80% of the $R^{11}$ residues is ethyl and at least 80% of the $R^{21}$ residues is methyl; or
  at least 80% of the $R^{11}$ residues is n-butyl and at least 80% of the $R^{21}$ residues is methyl; or
  at least 80% of the $R^{11}$ residues is n-butyl and at least 80% of the $R^{21}$ residues is ethyl.

Another aspect of the present invention relates to a method of preparing a statistical copolymer, said method comprising cationic ring-opening polymerization of a monomeric reaction mixture comprising an optionally 2-substituted 2-oxazoline and an optionally 2-substituted 2-oxazine in a molar ratio in the range of 3:97 to 97:3, wherein the optional substituent in the 2-position of the 2-substituted-2-oxazoline is a residue $R^{11}$ as defined herein before, and the optional substituent in the 2-position of the 2-substituted-2-oxazine is a residue $R^{21}$ as defined herein before.

According to a preferred embodiment, the monomeric reaction mixture comprises the optionally 2-substituted 2-oxazoline and the optionally 2-substituted 2-oxazine in a molar ratio in the range of 5:95 to 95:5, more preferably in a molar ratio in the range of 20:80 to 80:20.

Preferably, the monomeric reaction mixture contains a 2-substituted 2-oxazoline and/or a 2-substituted 2-oxazine. More preferably, the reaction mixture contains 2-substituted 2-oxazoline and a 2-substituted 2-oxazine.

The cationic ring-opening polymerization is preferably carried out in the presence of a cationic polymerization initiator, especially an electrophilic agent as is known in the state of the art. Examples of suitable cationic polymerization initiators include alkyl halides, alkyl sulfonates, acyl halides, sulfonic acids and oxazolinium salts.

In the present method the copolymerization reaction is preferably terminated by reacting the copolymer with a nucleophilic agent as commonly used in the state of the art. Examples include water, amines (ammonia, primary, secondary, tertiary), carboxylates, thiolates, alkoxides, azide phthalimide and hydroxide. The nucleophilic agent can be added when the reaction mixture still contains monomeric reactants.

The monomeric reaction mixture preferably contains at least 20 wt. % of a commonly applied solvent, such as acetonitrile, butyronitrile, chlorobenzene, dichloromethane, chloroform, sulfolane, nitromethane, nitrobenzene, anisole and mixtures thereof. More preferably, the reaction mixture contains at least 40 wt. % of a solvent selected from acetonitrile, chlorobenzene and mixtures thereof.

The copolymerization of the oxazoline and oxazine monomers in the present method is preferably carried out at a temperature in the range of 40 to 200° C., more preferably at a temperature in the range of 80 to 160° C.

In accordance with a particularly preferred embodiment of the present method, the statistical copolymer that is formed in the reaction mixture is hydrolysed by removing at least 50%, more preferably at least 70% and most preferably at least 90% of the pendant acyl residues. Hydrolysis of the acyl residues yields a polycationic polymer that is ideally suited for use in polyplexes.

A further aspect of the invention relates to a delivery system comprising a random copolymer as defined herein before, and a therapeutic agent that is non-covalently bound to said copolymer, wherein the therapeutic agent is selected from the group consisting of a gene, DNA, RNA, siRNA, miRNA, isRNA, agRNA, smRNA, a nucleic acid, a peptide, a protein, a chemotherapeutic agent, a hydrophobic drug, and a small molecule drug. The binding of the therapeutic agent to the random copolymer enables efficient transfer of the therapeutic agent into cells with low cytotoxicity.

Preferably, the therapeutic agent has a charge at a predetermined pH in the range of 6.5 to 8; and the random copolymer polymer has an opposite charge than the therapeutic agent at predetermined pH, an electrostatic bond being formed between the therapeutic agent and the random copolymer at the predetermined pH. Preferably, the therapeutic agent has a negative charge at the aforementioned predetermined pH, whereas the copolymer has a positive charge at the same predetermined pH.

In a preferred embodiment, the therapeutic agent that is bound to the random copolymer is selected from a gene, DNA, RNA, siRNA, miRNA, isRNA, agRNA and smRNA.

The delivery system containing the random copolymer and the therapeutic agent can suitably be used in therapeutic treatment, said treatment preferably comprising parenteral administration of the delivery system.

Yet another aspect micellar drug delivery system comprising a gradient copolymer as defined herein before, and a drug that is non-covalently bound to said copolymer.

Polymer micelles are nanoparticles that, when formed in water, typically have a hydrophilic polymer chain as a shell and a hydrophobic polymer chain as a core. Accordingly, the gradient copolymer of the present invention preferably comprises a hydrophobic segment as well as a hydrophilic segment. Preferably, the drug in the micellar drug delivery system is a drug that is non-covalently bound to the hydrophobic polymer chain in the core of the micelle.

The delivery system containing the gradient copolymer and the drug can suitably be used in therapeutic treatment, said treatment preferably comprising oral administration of the drug delivery system.

Examples of drugs that may be incorporated in the micellar drug delivery system of the present invention include Exemestance (aromasin), Camptosar (irinotecan), Ellence (epirubicin), Femara (Letrozole), Gleevac (imatinib mesylate), Lentaron (formestane), Cytadren/Orimeten (aminoglutethimide), Temodar, Proscar (finasteride), Viadur (leuprolide), Nexavar (Sorafenib), Kytril (Granisetron), Taxotere (Docetaxel), Taxol (paclitaxel), Kytril (Granisetron), Vesanoid (tretinoin) (retin A), XELODA (Capecitabine), Arimidex (Anastrozole), Casodex/Cosudex (Bicalutamide), Faslodex (Fulvestrant), Iressa (Gefitinib), Nolvadex, Istubal, Valodex (tamoxifen citrate), Tomudex (Raltitrexed), Zoladex (goserelin acetate), Leustatin (Cladribine), Velcade (bortezomib), Mylotarg (gemtuzumab ozogamicin), Alimta (pemetrexed), Gemzar (gemcitabine hydrochloride), Rituxan (rituximab), Revlimid (lenalidomide), Thalomid (thalidomide), Alkeran (melphalan), Adriamycin (doxorubicin), Cerubidine (daunorubicin), paclitaxel, curcumin and derivatives thereof.

The invention is further illustrated by the following non-limiting examples.

EXAMPLES

Materials

All manipulations concerning the preparation of polymerization mixtures until capping of the microwave vials were carried out in a VIGOR Sci-Lab SG 1200/750 Glovebox System with a water concentration≤0.1 ppm.

For the polymerizations, a Biotage Initiator EXP Microwave System with Robot Sixty was used. During the polymerization the microwave synthesizer operated at a constant set temperature (140° C.), which was monitored by an IR-sensor.

GC was performed on an Agilent 7890A system equipped with a VWR Carrier-160 hydrogen generator and an Agilent HP-5 column of 30 m length and 0.320 mm diameter. An FID detector was used and the inlet was set to 240° C. with a split injection of ratio 25:1. Hydrogen was used as carrier gas at a flow rate of 2 mL/min. The oven temperature was increased with 20° C./min from 50° C. to 120° C., followed by a ramp of 50° C./min. to 240° C.

General Procedure to Determine Copolymerization Kinetics

A stock solutions was made containing both monomers (total monomer concentration of 4 M, 2 M per individual monomer), initiator (methyl tosylate, aiming at DP 100 at full conversion or 50 repeating units of each monomer) and solvent (dry acetonitrile).

This mixture was divided equally (700 μL) over 0.5-2 ml biotage vials with triangle stir bars, capped and heated up to 140° C., in the microwave. Polymerization was halted by cooling down the vials after different time intervals.

The samples were diluted with chloroform and stirred for at least 1 h before taking samples for GC analysis. The conversion was determined by GC with the solvent acetonitrile as internal standard and using the ratio of monomer to solvent of a sample taken of the stock solution as time zero for comparison.

From the slope of the kinetic plots, the polymerization rate constants for the two individual monomers were calculated and these polymerization rate constants were then used to calculate the composition of a chain of 100 repeat units by assigning the Ox of Oz repeat units on the basis of the monomer conversions. These schematic plots of the polymers represented by 100 repeating spheres were then used to calculate the [Oz]/[Ox] ratio of the Ini fragment and the Nuc fragment. This calculation method is described by Lobert et al. (*Amphiphilic gradient copolymers containing fluorinated 2-phenyl-2-oxazolines: Microwave-assisted one-pot synthesis and self-assembly in water*, J Polym Sci, Part A, Polym Chem 2008, 46, 5859-5868).

Example 1

2-Methyl-2-oxazoline (MeOx) and 2-methyl-2-oxazine (MeOZi) were polymerized as described in the general method. The analysis of this copolymerization led to the kinetic plot shown in FIG. 1, illustrating the unexpected reversed copolymerization behavior.

Figure 2:
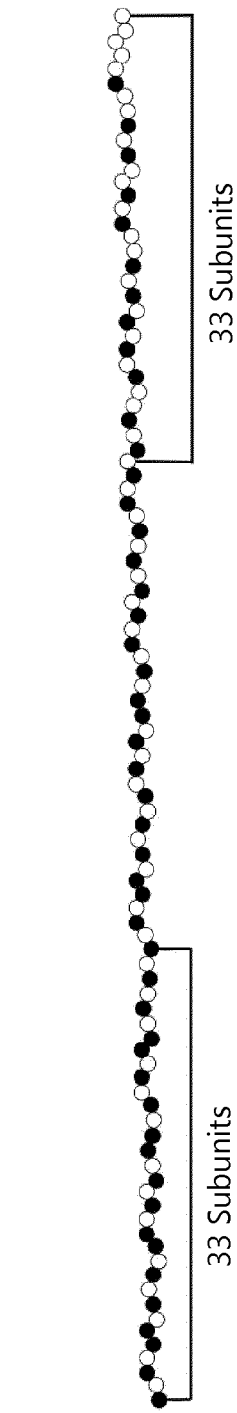
FIG. 2 is a gradient analysis of the Ini and Nuc fragments of the polymer of FIG. 1.

The gradient analysis depicted in FIG. 2 revealed that the ini fragment of the polymer contained 19 units MeOZi (black) and 14 units MeOx (white) while the Nuc fragment contains 12 units MeOZI and 21 units MeOx. Thus, the [Oz]/[Ox] ratio of Ini fragment over that of the Nuc fragment equals 2.375, indicative of gradient monomer distribution.

Example 2

Figure 3:
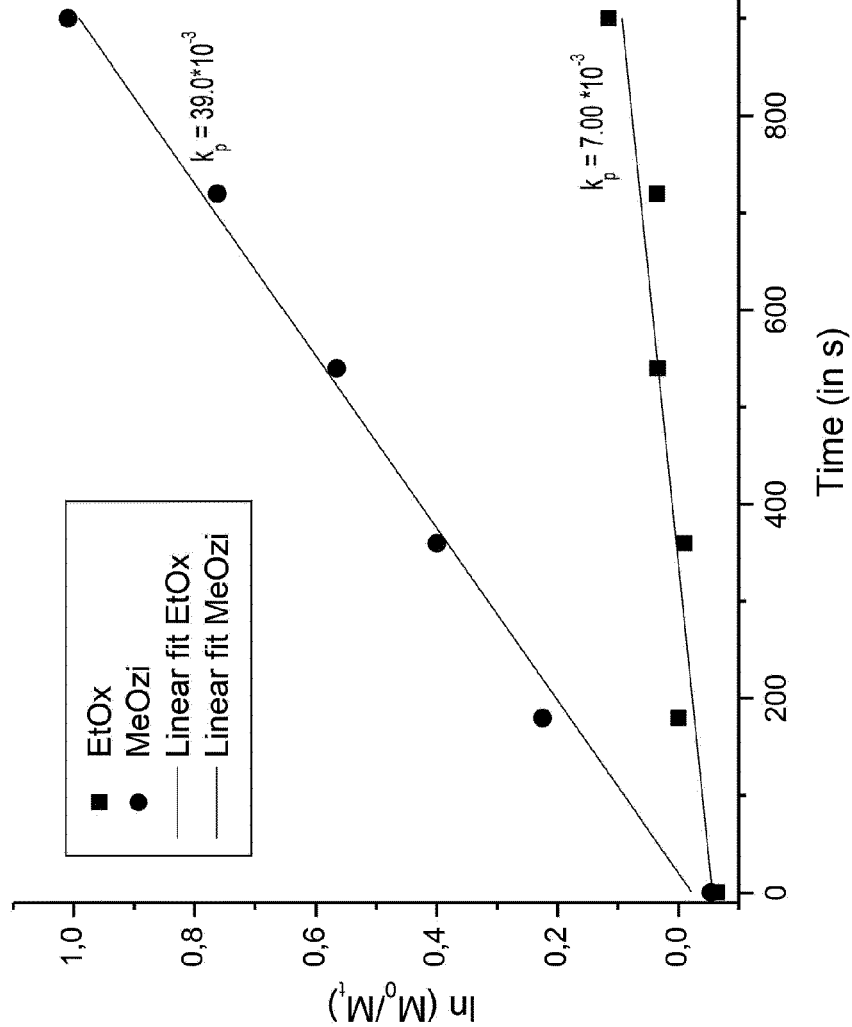
FIG. 3 is a kinetic plot of one copolymerization of 2-Ethyl-2-oxazoline (EtOx) and 2-methyl-2-oxazine (MeOZi).

2-Ethyl-2-oxazoline (EtOx) and 2-methyl-2-oxazine (MeOZi) were polymerized as described in the general method. The analysis of this copolymerization led to the kinetic plot shown in FIG. 3, illustrating the unexpected reversed copolymerization behavior.

Figure 4:
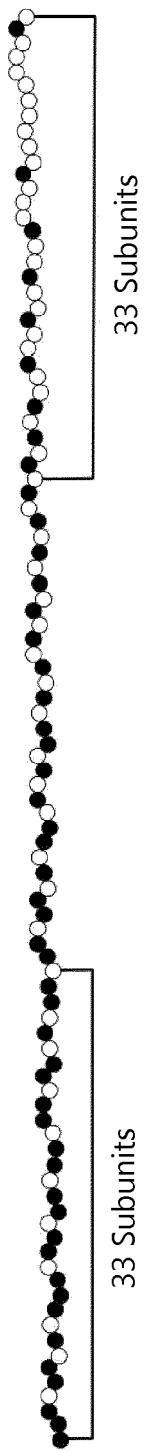
FIG. 4 is a gradient analysis of the Ini and Nuc fragments of the polymer of FIG. 3.

The gradient analysis depicted in FIG. 4 revealed that the Ini fragment of the polymer contained 22 units MeOZi (black) and 11 units EtOx (white) while the Nuc fragment has 9 units MeOZI and 24 units EtOx. This gives an [Oz]/[Ox] ratio of Ini fragment over Nuc fragment of 5.33 indicating gradient monomer distribution.

Example 3

Figure 5:
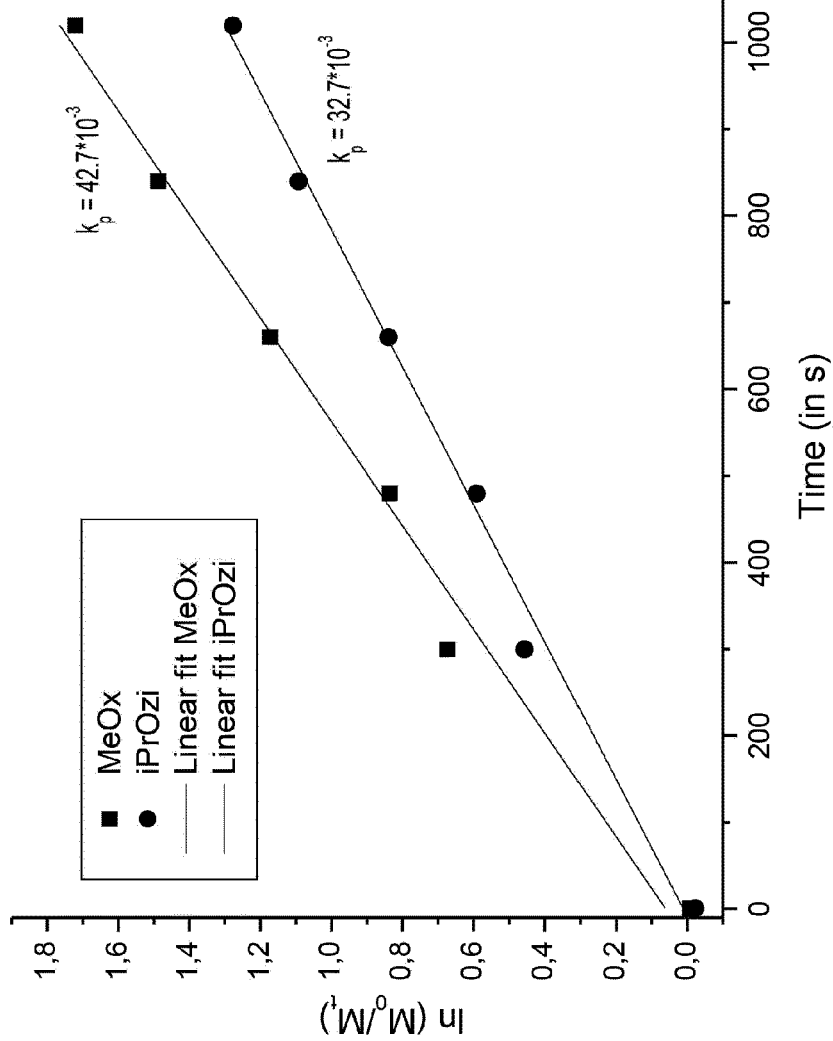
FIG. 5 is kinetic plot of one copolymerization of 2-Methyl-2-oxazoline (MeOx) and 2-iso-propyl-2-oxazine (iprpOZi).

2-Methyl-2-oxazoline (MeOx) and 2-iso-propyl-2-oxazine (ipropOZi) were polymerized as described in the general method. The analysis of this copolymerization led to the kinetic plot shown in FIG. 5.

Figure 6:
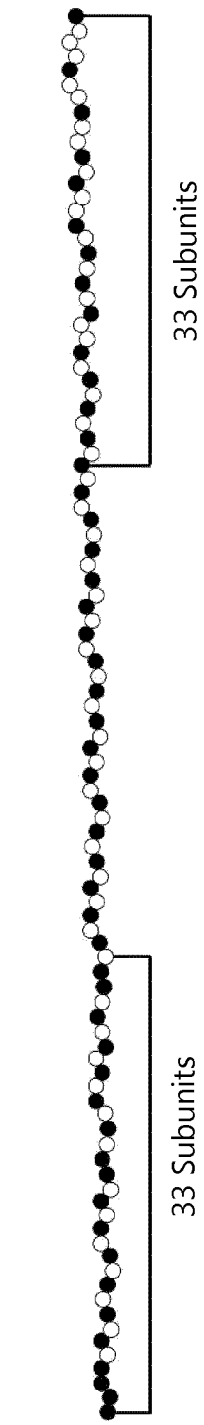
FIG. 6 is a gradient analysis of the Ini and Nuc fragments of the polymer of FIG. 5.

The gradient analysis depicted in FIG. 6 revealed that the Ini fragment of the copolymer contained 14 units ipropOZi (white) and 19 units MeOx (black) while the Nuc fragment has 19 units ipropOZi and 14 units MeOx. This gives an [Oz]/[Ox] ratio of Ini fragment over Nuc fragment of 0.54, indicating random monomer distribution.

Example 4

Figure 7:
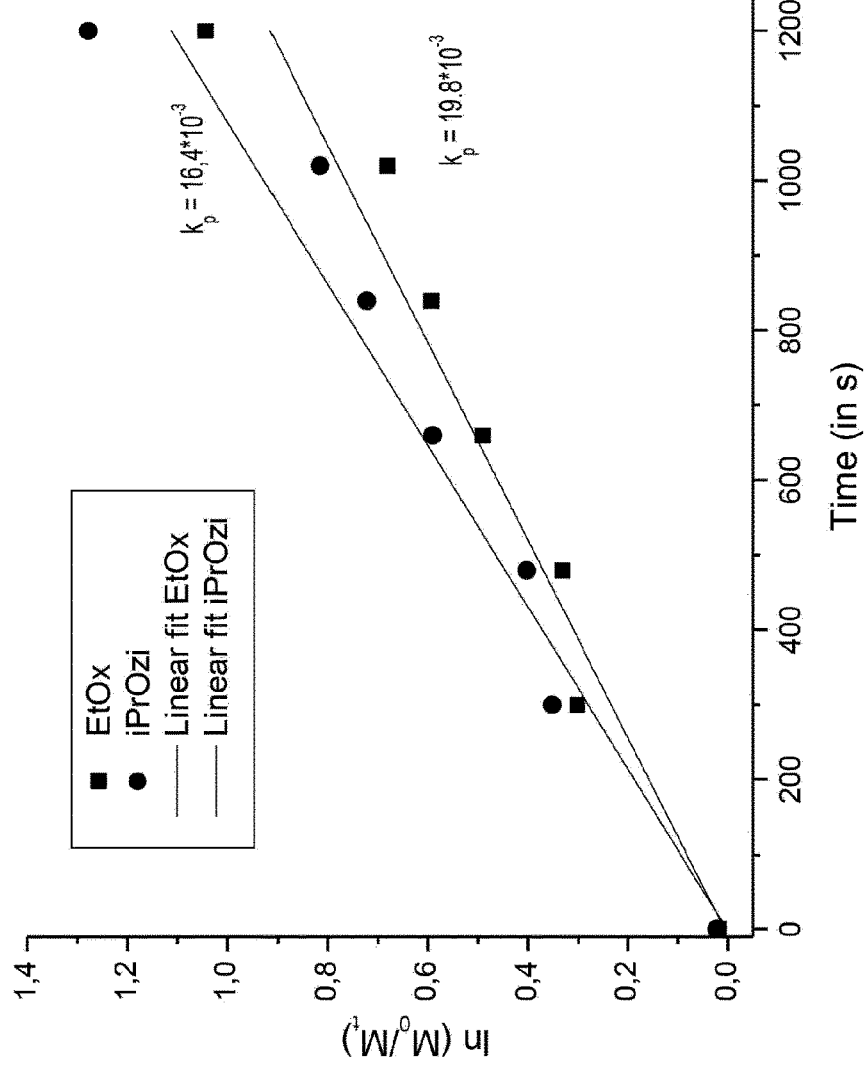
FIG. 7 is a kinetic plot of one copolymerization of 2-Ethyl-2-oxazoline (EtOx) and 2-iso-propyl-2-oxazine (ipropOZi).

2-Ethyl-2-oxazoline (EtOx) and 2-iso-propyl-2-oxazine (ipropOZi)) were polymerized as described in the general method. The analysis of this copolymerization led to the kinetic plot shown in FIG. 7, illustrating the unexpected reversed copolymerization behavior.

Figure 8:
FIG. 8 is a gradient analysis of the Ini and Nuc fragments of the polymer of FIG. 7.

The gradient analysis depicted in FIG. 8 revealed that the Ini fragment of the copolymer contained 18 units ipropOZi (black) and 15 units EtOx (white) while the Nuc fragment has 15 units ipropOZi and 18 units EtOx. This gives an [Oz]/[Ox] ratio of Ini fragment over Nuc fragment of 1.44 indicating random like monomer distribution.

Example 5

Figure 9:
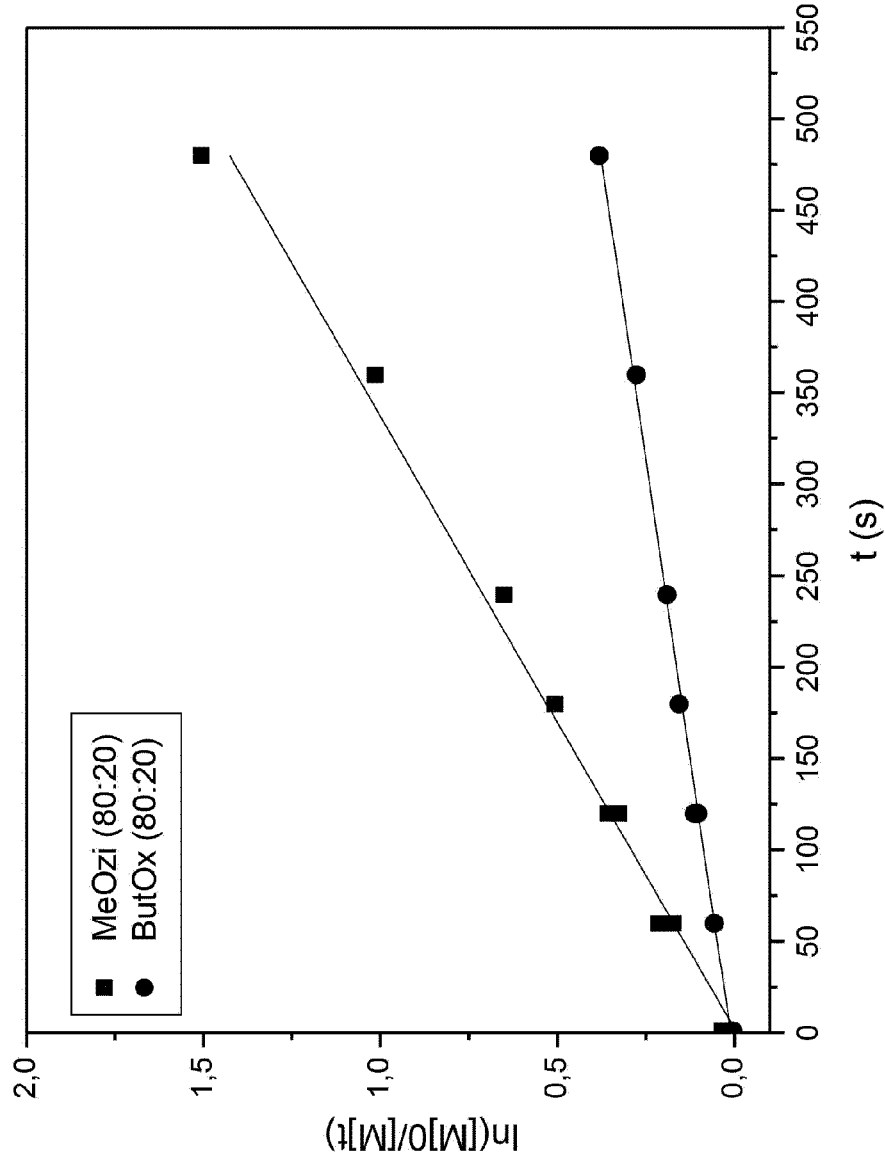
FIG. 9 is a kinetic plot of one copolymerization of 2-Butyl-2-oxazoline (ButOx) and 2-methyl-2-oxazine (MeOZi).

2-Butyl-2-oxazoline (ButOx) and 2-methyl-2-oxazine (MeOZO were polymerized in a slightly modified procedure compared the general method. Instead of a 1:1 ratio of monomer, a 2:8 (ButOx:MeOZi) was used. The analysis of this copolymerization led to the kinetic plot shown in FIG. 9, illustrating the unexpected reversed copolymerization behavior.

Figure 10:
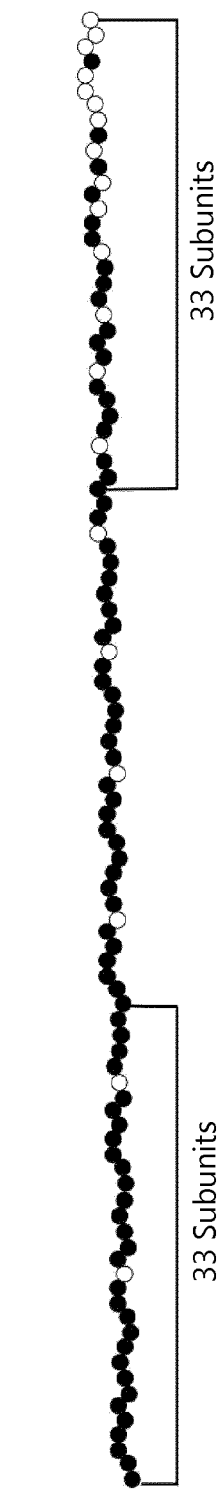
FIG. 10 is a gradient analysis of the Ini and Nuc fragments of the polymer of FIG. 9.

The gradient analysis depicted in FIG. 10 revealed that Ini fragment of the copolymer contained 31 units MeOZi (black) and 2 units ButOx (white) while the Nuc fragment has 19 units MeOZI and 14 units ButOx. This gives an [Oz]/[Ox] ratio of Ini fragment over Nuc fragment of 11.42, indicating gradient monomer distribution.

Example 6

Figure 11:
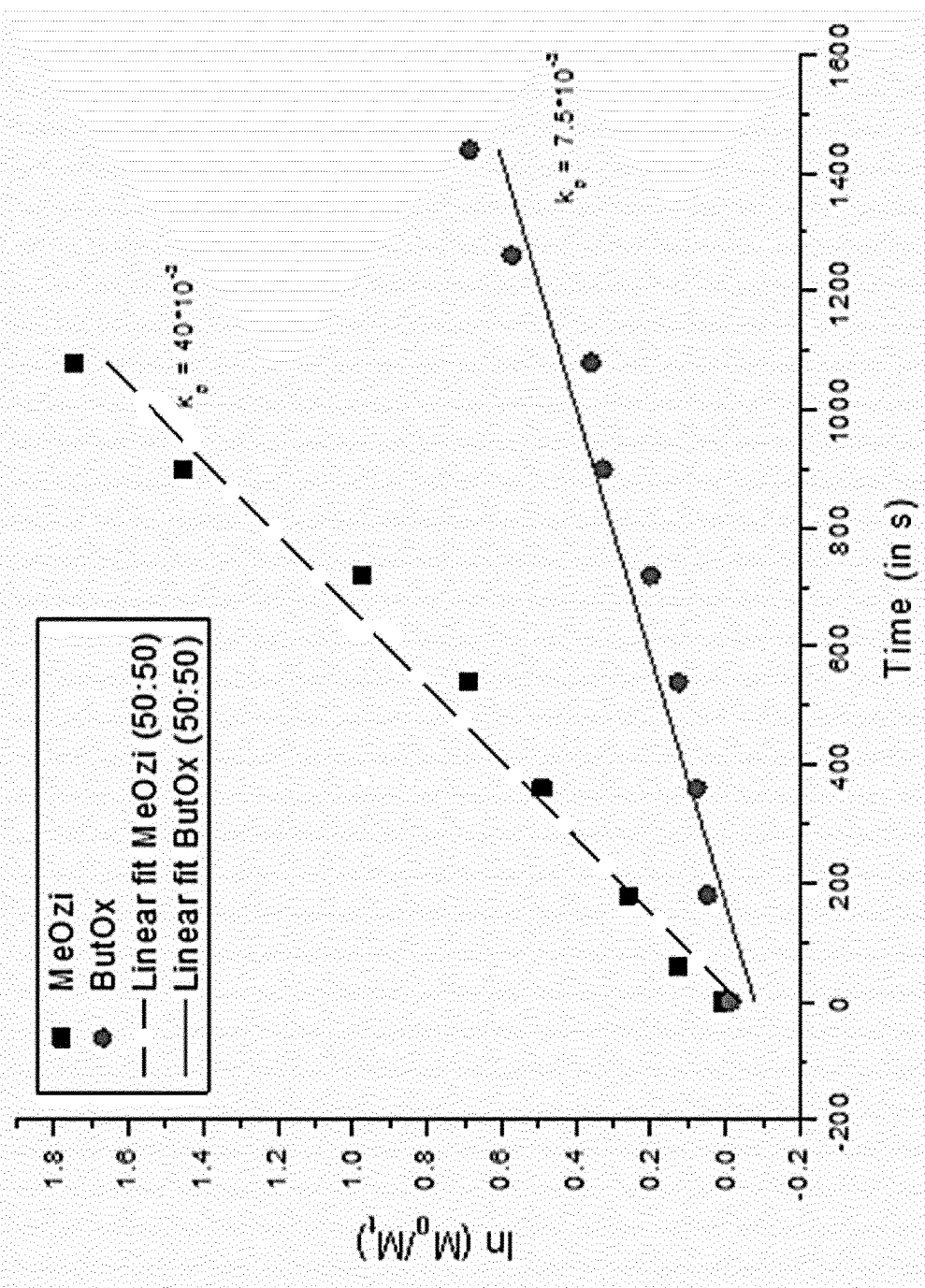
FIG. 11 is a kinetic plot of another copolymerization of 2-Butyl-2-oxazoline (ButOx) and 2-methyl-2-oxazine (MeOZi).

2-Butyl-2-oxazoline (ButOx) and 2-methyl-2-oxazine (MeOZO were polymerized as described in the general method. The analysis of this copolymerization led to the kinetic plot shown in FIG. 11, illustrating the unexpected reversed copolymerization behavior.

Figure 12:
FIG. 12 is a gradient analysis of the Ini and Nuc fragments of the polymer of FIG. 11.

The gradient analysis depicted in FIG. 12 revealed that Ini fragment of the copolymer contained 22 units MeOZi (black) and 11 units ButOx (white) while the Nuc fragment has 8 units MeOZI and 25 units ButOx. This gives an [Oz]/[Ox] ratio of Ini fragment over Nuc fragment of 6.25, indicating gradient monomer distribution.

Example 7

Figure 13:
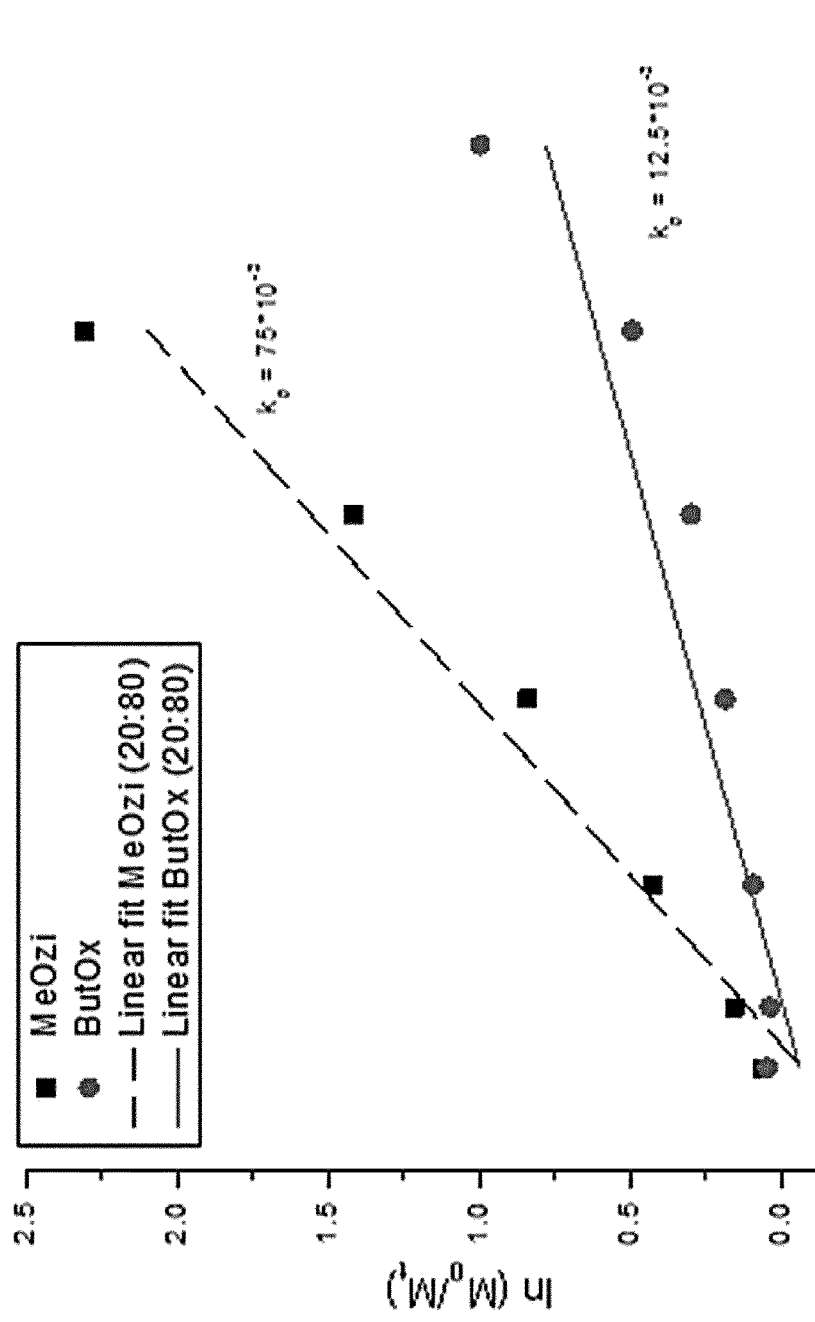
FIG. 13 is a kinetic plot of yet another copolymerization of 2-Butyl-2-oxazoline (ButOx) and 2-methyl-2-oxazine (MeOZi).

2-Butyl-2-oxazoline (ButOx) and 2-methyl-2-oxazine (MeOZO were polymerized in a slightly modified procedure compared the general method. Instead of a 1:1 ratio of monomer a 8:2 (ButOx:MeOZi) was used. The analysis of this copolymerization led to the kinetic plot shown in FIG. 13, illustrating the unexpected reversed copolymerization behavior.

Figure 14:
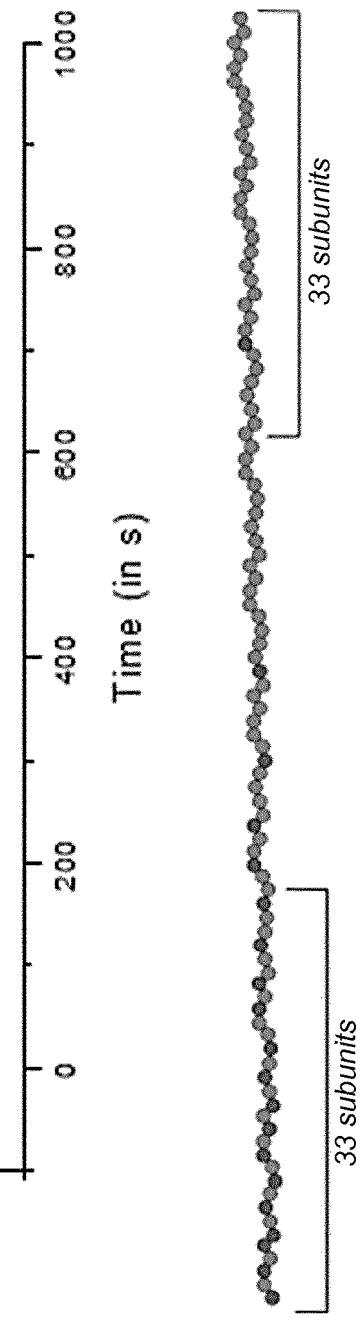
FIG. 14 is a gradient analysis of the Ini and Nuc fragments of the polymer of FIG. 13.

The gradient analysis depicted in FIG. 14 revealed that Ini fragment of the copolymer contained 15 units MeOZi (black) and 18 units ButOx (white) while the Nuc fragment has 1 unit MeOZI and 32 units ButOx. This gives an [Oz]/[Ox] ratio of Ini fragment over Nuc fragment of 26.67, indicating gradient monomer distribution.

Example 8

The gradient copolymer of Examples 5 and 6 were used to load Rhodamine octadecylester (dye). Therefore, polymer micelles were prepared in water (10 mg/mL) by direct dissolution in water (polymer from example 5) or by solvent displacement by first dissolving the polymer in ethanol followed by addition of water and dialysis (polymer from example 6). The dye was dissolved in ethanol (10 mg/mL) and 100 μL of the dye solution was added to 1 mL of the polymer solution followed by removal of the ethanol by dialysis.

The uptake of the dye in the copolymer particles was determined by dispersing the loaded particles in demineralized water to provide a total dye concentration of 2.50 μg/ml and measuring the absorption at 561 nm. This absorption was compared to the absorption of a reference solution having the same dye content, but not containing copolymer. From this data the % dye loading was calculated.

The results of these measurements are shown in Table 1.

TABLE 1

| Copolymer | Absorption | Dye concentration (μg/ml) | % dye loading |
|---|---|---|---|
| Example 5 | 0.088 | 2.09 | 83.8 |
| Example 6 | 0.074 | 1.69 | 67.6 |

Example 9

The (hydrolysed) random copolymer of Example 4 was used to prepare a polyplex of pDNA and this polyplex was used to transfect human ovarian cancer cells.

The copolymer was hydrolysed by dissolving 1 gram of polymer in 7.5 mL deionized water and 7.5 mL hydrochloric acid (HCl; concentrated HCl solution), followed by heating in closed vials at 140° C. for 9 hours in a Biotage™ microwave. After this, the polymer was diluted with deionized water and the HCl and deionized water were evaporated with reduced pressure. The samples were neutralized with a 2M sodiumhydroxide (NaOH) solution in water and freeze dried. NMR analysis confirmed near quantitative hydrolysis.

A polymer solution of 1 mg/mL was prepared in deionized water. The polymer solution was sterilized via filtration with a 0.22 μm filter and was diluted to 0.1 mg/mL in DPBS. Polyplexes were prepared by adding polymer solution onto the pDNA. Polyplexes with different N/P ratios were prepared: 2.5, 5, 10, 25 and 50. A control polyplex solution was prepared with B-PEI with a N/P ratio of 10. The polyplexes were left to stabilize for 10 minutes.

A cell suspension of $8.0*10^4$ cells/mL in medium containing 10% FBS was prepared. A 24-wells plate (Greiner) was seeded with 400 μL cell suspension. The plate was incubated at 37° C. with air containing 5% $COL_2$ for 24 hours.

Next, 150 μL polyplex solution was added to wells with 150 μL fresh medium with or without FBS. 2 rows of wells were filled with 150 μL DPBS instead of polyplexes as a control. After 1 hour, medium was replaced by fresh medium containing 10% FBS. The cells were incubated at 37° C. with air containing 5% $COL_2$. After 48 hours, transfection efficiency was analyzed by FACS and imaged using fluorescence microscopy.

For FACS analysis the cells were trypsinized with 300 μL of 0.25% trypsin per well. The trypsin was deactivated with 2 mL of medium containing 10% FBS per well. The cells were transferred to FACS tubes and centrifuged for 5 minutes at 600 rcf. The supernatant was decanted. The cell pellet was loosened by rasping over a metal grid and 200 μL of DPBS was added to the FACS tubes. Fluorescence intensity was measured using FACS Calibur (Becton-Dickinson). The acquired data was analyzed using Flowing Software.

The results showed that the transfection efficiency of the hydrolysed copolymer of 2-Ethyl-2-oxazoline and 2-isopropyl-2-oxazine (PEI-PPI) equals or even exceeds the transfection efficiency of branched-polyethyleneimine (B-PEI). Furthermore, higher transfection efficiency was observed for these copolymers in presence of FBS in contrast to B-PEI.

The invention claimed is:

1. A gradient copolymer represented by the following formula (I):

wherein:
   (a) Ini represents a residue of an initiator of cationic polymerization;
   (b) Nuc represents a residue of a nucleophilic agent;
   (c) Ox represents $N(R^1)CHR^aCHR^a$; each $R^1$ independently represents H or $C(O)R^{11}$; and $R^{11}$ independently represents optionally substituted $C_{1-12}$ alkyl, optionally substituted cycloalkyl, optionally substituted aralkyl or optionally substituted aryl;
   (d) Oz represents $N(R^2)CHR^aCHR^aCHR^a$; each $R^2$ independently represents $C(O)R^{21}$ or H; and $R^{21}$ independently represents optionally substituted $C_{1-12}$ alkyl, optionally substituted cycloalkyl, optionally substituted aralkyl or optionally substituted aryl;
   (e) each $R^a$ independently represents H, linear or branched $C_{1-3}$ alkyl;
   (f) m≥5;
   (g) n≥5;
   (h) m+n≥20;
   (i) 3:97≤m:n≤97:3;
   wherein the copolymer comprises three fragments of equal size, a fragment adjacent Ini (Ini fragment), a fragment adjacent Nuc (Nuc fragment) and a central fragment that separates the Ini fragment and the Nuc fragments, wherein the monomer ratio [Oz]/[Ox] in the Ini-half of the copolymer is at least 2 times higher or lower than the same ratio in the Nuc-half of the copolymer.

2. The copolymer according to claim 1, wherein Ra represents H.

3. The copolymer according to claim 1, wherein 10≤m≤250.

4. The copolymer according to claim 1, wherein 10≤n≤250.

5. The copolymer according to claim 1, wherein each $R^{21}$ independently represents optionally substituted C1-9 alkyl.

6. The copolymer according to claim 1, wherein each $R^{11}$ independently represents optionally substituted $C_{1-9}$ alkyl or cyclopropyl.

7. A method of preparing a gradient copolymer according to claim 1, comprising cationic ring-opening polymerizing of a monomeric reaction mixture comprising an optionally 2-substituted 2-oxazoline and an optionally 2-substituted 2-oxazine in a molar ratio in the range of 3:97 to 97:3, wherein the optional substituent in the 2-position of the 2-substituted-2-oxazoline is a residue $R^{11}$ as defined in claim 1, and the optional substituent in the 2-position of the 2-substituted-2-oxazine is a residue $R^{21}$ as defined in claim 1.

8. The method according to claim 7, wherein the cationic ring-opening polymerization is carried out in the presence of a cationic polymerization initiator selected from alkyl halides, alkyl sulfonates, acyl halides, oxazolinium salts or sulfonic acids.

9. The method according to claim 7, wherein the copolymer comprises pendant acyl residues and at least 50% of the pendant acyl residues are removed by hydrolysis.

10. A micellar drug delivery system comprising a gradient copolymer according to claim 1 and a drug that is non-covalently bound to the copolymer.

11. A method of preparing a statistical copolymer, said method comprising cationic ring-opening polymerization of a monomeric reaction mixture comprising an optionally 2-substituted 2-oxazoline and an optionally 2-substituted 2-oxazine in a molar ratio in the range of 3:97 to 97:3, wherein the optional substituent in the 2-position of the 2-substituted-2-oxazoline is a residue $R^{11}$ as defined in claim 1, and the optional substituent in the 2-position of the 2-substituted-2-oxazine is a residue $R^{21}$ as defined in claim 1, wherein the statistical copolymer that is formed in the reaction mixture comprises pendant acyl residues, and wherein the statistical polymer is hydrolysed by removing at least 50% of the pendant acyl residues.

* * * * *